United States Patent [19]

Purcell et al.

[11] Patent Number: 4,810,723
[45] Date of Patent: Mar. 7, 1989

[54] DIBENZO[B,E]OXEPINACETIC ACID DERIVATIVES AND PHARMACEUTICAL COMPOSITIONS CONTAINING THEM

[75] Inventors: Thomas Purcell, Montfort l'Amaury; Luc Rivron, Asnieres; Lydia Zard, Gif sur Yvette, all of France

[73] Assignee: Synthelabo, France

[21] Appl. No.: 135,236

[22] Filed: Dec. 21, 1987

[30] Foreign Application Priority Data

Dec. 22, 1986 [FR] France ............... 86 17990

[51] Int. Cl.$^4$ ............... C07D 313/12; A61K 31/335
[52] U.S. Cl. .................... 514/450; 549/354
[58] Field of Search ............ 549/354; 514/450

[56] References Cited

U.S. PATENT DOCUMENTS 4,356,186 10/1982 Uno et al. ............... 514/450
4,585,788 4/1986 Helsley et al. .......... 514/450
4,701,466 10/1987 Purcell et al. .......... 549/354

*Primary Examiner*—Alan L. Rotman
*Assistant Examiner*—Zinna Northington
*Attorney, Agent, or Firm*—Wegner & Bretschneider

[57] ABSTRACT

A compound, in the form of a pure optical isomer or a racemate, which is a dibenzo[be]oxepinacetic acid of the general formula (I)

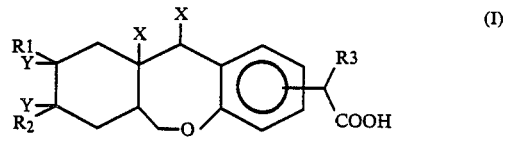

in which R1, R2 and R3, which may be the same or different, each represent hydrogen or methyl, XX represents a carbon-carbon bond or two hydrogen atoms, and YY represents a carbon-carbon bond or two hydrogen atoms, or a pharmaceutically acceptable salt thereof has useful therapeutic properties, especially as an anti-inflammatory.

3 Claims, No Drawings

DIBENZO[B,E]OXEPINACETIC ACID DERIVATIVES AND PHARMACEUTICAL COMPOSITIONS CONTAINING THEM

The present invention relates to compounds which are dibenzo[be]oxepinacetic acid derivatives or salts thereof, their preparation and pharmaceutical compositions containing them.

The invention provides a compound which is a dibenzo(b,e)oxepinacetic acid of formula (I)

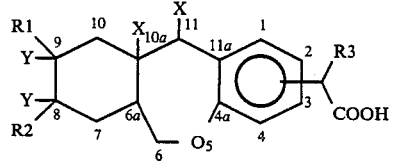

in which R1, R2 and R3, which may be the same or different, each represent hydrogen or methyl, XX represents a carbon-carbon bond or two hydrogen atoms, and YY represents a carbon-carbon bond or two hydrogen atoms, or a pharmaceutically acceptable salt thereof.

The various stereoisomeric forms, i.e. pure optical isomers or mixtures thereof, that can be taken by the compounds of formula (I) also form part of the invention. In particular, when XX denotes two hydrogen atoms, there is cis or trans isomerism with respect to the axis defined by the atoms 6a and 10a.

According to the invention, the compounds may be prepared according to Scheme 1 on the following page.

SCHEME 1

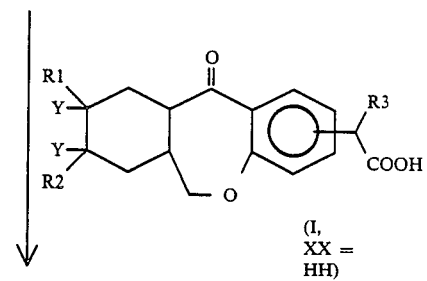

In accordance with this scheme, compounds of the invention are prepared by a process which comprises:

(a) hydrolysing an ester of formula (II)

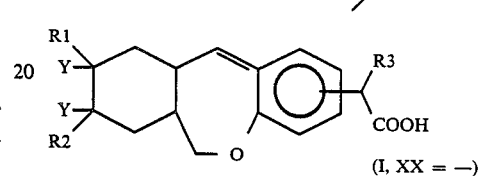

(wherein the various symbols are as defined above) to form a free acid of formula (III)

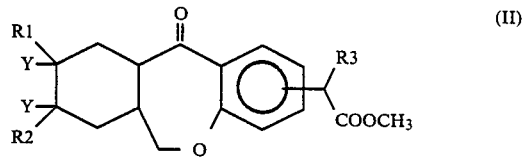

(b) reducing the ketone group of free acid (III) to an alcohol group to form an alcohol of formula (IV)

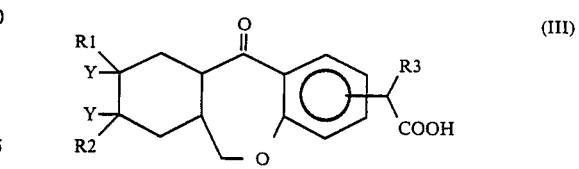

(c) either (i) dehydrating the alcohol (IV) to provide an acid of formula (I) in which XX represents a carbon-carbon bond and optionally catalytically hydrogenating said bond to provide a said acid in which XX represents two hydrogen atoms, or (ii) reducing the alcohol (IV) to provide an acid of formula (I) in which XX represents two hydrogen atoms, (d) optionally if desired methylating a resulting compound of formula (I) in which R3 represents hydrogen so as to provide a compound of formula (I) in which R3 represents methyl, and (e) if desired converting a free acid of formula (I) into a pharmaceutically acceptable salt thereof.

The starting esters of formula (II) in which YY represents a carbon-carbon bond are described in EP-A No. 0,198,762.

If it is desired to prepare compounds (I) in the formula of which YY represents two hydrogen atoms, an ester (II, YY=—) may first be subjected to catalytic hydrogenation, for example under pressure in the presence of a catalyst such as platinum dioxide.

The ester of formula (II) is hydrolysed, for example with sodium hydroxide in alcoholic medium, to obtain a free acid of formula (III). The acids (and their esters) of formula (III) in which YY denotes two hydrogen atoms and R1 and R2 denote two hydrogen atoms are also described in EP-A No. 0,037,254.

According to this document, they are obtained by a process illustrated by Scheme 2 on the following page.

SCHEME 2

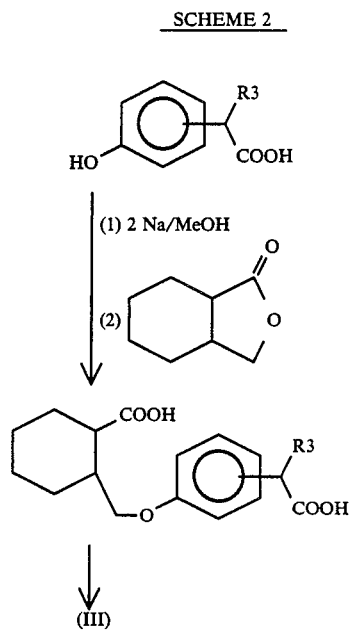

A benzeneacetic acid of formula (V) is treated with sodium and the salt thereby obtained is reacted with a lactone, octahydro-1-isobenzofuranone, of formula (VI), which gives the derivative of formula (VII) which is subjected to cyclization to provide the ester (III).

If the lactone of formula (VI) has a specified stereochemical structure, this leads to an intermediate of formula (III), and finally to a compound of formula (I), which themselves have specified stereochemical structures.

The lactone of formula (VIa) is described in Organic Syntheses (1985), 63, 10 and that of formula (VIb) may be synthesized from the diacid of formula (VIc) described in J. Org. Chem. (1963), 28, 48, passing via the corresponding anhydride, according to methods similar to those described in J. Org. Chem. (1964), 29, 3154 and J. Org. Chem. (1970), 35, 3574.

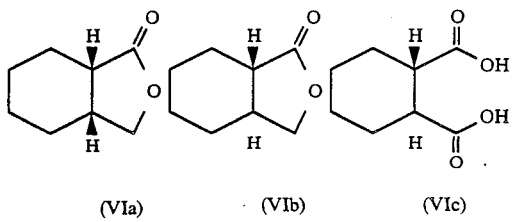

The ketone group of the compound (III) may be reduced to a secondary alcohol group by means of alkali metal borohydride. The alcohol of formula (IV) thereby obtained can then be treated in two different ways, depending on whether it is desired to prepare a compound (I) in the formula of which XX denotes a carbon-carbon bond or two hydrogen atoms.

Thus, on the one hand, the alcohol (IV) can be dehydrated, for example in the presence of para-toluenesulphonic acid, in the heated state and in a solvent such as benzene, thereby leading to a compound of formula (I) in which XX denotes a carbon-carbon bond.

It is possible, on the other hand, to reduce the alcohol (IV), for example in the presence of sodium cyanoborohydride and zinc iodide, at room temperature and, for example, in a halogenated solvent, thereby providing a compound of formula (I) in which XX denotes two hydrogen atoms. This reduction does not epimerize the 10a centre, the stereochemistry of the final compound being determined by that of the starting compound.

It is also possible to proceed from a compound of formula (I) in which XX denotes a bond to a compound of formula (I) in which XX and YY denote HH by subjecting the former compound to a catalytic hydrogenation under pressure, for example in a solvent such as ethanol and in the presence of palladinized charcoal. This hydrogenation is not stereoselective with respect to the sides of the bond 10a—11, and gives a 50:50 mixture of cis and trans isomers with respect to the bond 6a–10a.

Finally, a compound of formula (I) in which R3 denotes a methyl group may be prepared from a compound of formula (1) in which R3 denotes hydrogen by protecting the latter beforehand by esterification using a lower alcohol, for example methanol, at the refluxing temperature, then alkylating the ester thereby obtained, for example using a halide such as iodomethane in the presence of lithium diisopropylamide (prepared in situ using diisopropylamine and n-butyllithium), in a solvent such as tetrahydrofuran, and then reconverting to the acid by hydrolysing the ester thereby obtained, for example with aqueous sodium hydroxide, in the heated state and in alcoholic medium.

The Examples which follow illustrate the preparation of a few compounds according to the invention.

The structures of the products obtained were confirmed by microanalyses and the IR and NMR spectra.

EXAMPLE 1

6,6a,7,8,9,10-Hexahydro(b,e)oxepin-3-acetic acid.

(a) Methyl 11-oxo-6,6a,7,8,9,10,10a,11-octahydrodibenzo(b,e)oxepin-3-acetate.

8.58 g (0.03 mole) of methyl 11-oxo-6,6a,7,10,10a,11-hexahydrodibenzo(b,e)oxepin-3-acetate, 1 g of platinum oxide and 200 ml of ethanol are introduced into a 500-ml hydrogenation vessel, and hydrogenation is performed at approximately 0.28 MPa for 45 minutes.

The catalyst is separated by filtration under argon and the filtrate is evaporated, and this leaves 8 g of an oil which is used in the following stage without further treatment.

(b) 11-Oxo-6,6a,7,8,9,10,10a,11-octahydrodibenzo(b,e)oxepin-3-acetic acid.

8 g of the oil obtained according to (1a) is treated at 60° C. for 1 h with a mixture of 100 ml of methanol, 100 ml of water and 4.5 ml of 30% strength sodium hydroxide solution. The alcohol is then evaporated off and the traces of residual ester are extracted with ethyl acetate. The aqueous phase is acidified with 1N hydrochloric acid and the organic acid extracted with ethyl acetate.

The organic phase is dried over magnesium sulphate, concentrated and distilled at between 185° and 190° C. at approximately 25 Pa. After recrystallization of the distillate in isopropyl alcohol, 6.5 g of solid are collected. m.p. 99°–101° C.

(c) 6,6a,7,8,9,10-Hexahydrodibenzo(b,e)oxepin-3-acetic acid.

5.48 g of the solid obtained according to 1(b) are dissolved in 100 ml of ethanol and 1.2 g of sodium borohydride is added slowly. The mixture is stirred for 40 minutes and then concentrated.

The residue is taken up with 200 ml of water, hydrochloric acid is added slowly to pH 2, the mixture being cooled in ice, and the product is extracted with ethyl acetate.

The solvent is evaporated off at 25° C. and the heat-sensitive product is rapidly taken up with 150 ml of benzene and 0.2 g of para-toluenesulphonic acid.

The water is driven off in a Dean and Stark apparatus in the space of approximately 30 minutes, the residue is concentrated at 40° C. under vacuum to a residual volume of approximately 15 ml, and the product is then purified on a silica column, eluting with a 95:5 dichloromethane/methanol mixture.

After recrystallization of the pure fractions in the cold in an 8:2 cyclohexane/isopropyl ether mixture, 2.5 g of the pure product are collected. m.p. 145°–147° C.

EXAMPLE 2

6,6a,7,10-Tetrahydrodibenzo[be]oxepin-3-acetic acid.

(a) 11-Hydroxy6,6a,7,10,10a,11-hexahydrodibenzo(b,e)oxepin-3-acetic acid.

2.72 g (0.01 mole) of 11-oxo-6,6a,7,10,10a,11-hexahydrodibenzo(b,e)oxepin-3-acetic acid and 200 ml of ethanol are introduced into a 1-L Erlenmeyer, and the solution is treated with 3 g of sodium borohydride at 0° C.

After 30 min of reaction, the mixture is evaporated, the residue taken up with water, and the suspension cooled in an icebath and treated with hydrochloric acid to pH 3 in order to destroy the excess sodium borohydride.

The alcohol obtained is extracted with ethyl acetate. After the organic phase has been dried over magnesium sulphate and evaporated, the residue is recrystallized in an 8:2 ethyl acetate/cyclohexane mixture. 2 g of crystals are obtained. m.p. 138°–140° C.

(b) 6,6a,7,10-Tetrahydrodibenzo[be]oxepin-3-acetic acid.

2.7 g of alcohol obtained according to 2(a) are subjected to dehydration in 300 ml of benzene under reflux, in the presence of 0.1 g of para-toluenesulphonic acid.

After 30 min, the benzene is evaporated off and the residue purified by chromatography on a silica column, eluting with a 9:1 methanol/dichloromethane mixture and recrystallizing the product obtained in a 7:3 petroleum ether/ethyl acetate mixture.

1.25 g of crystals are obtained. m.p. 120°–122° C.

EXAMPLE 3

6,6a,7,8,9,10,10a,11-Octahydrodibenzo(b,e)oxepin-3-acetic acid (50:50 cis/trans mixture).

3 g of the compound of Example 1, 250 ml of ethanol and 0.3 g of activated palladinized charcoal (10% palladium) are introduced into a Parr vessel, and hydrogenation is performed at approximately 0.28 MPa for 8 hours.

The catalyst is separated by filtration under argon, the solvent evaporated off and the residue recrystallized in a 6:4 cyclohexane/pentane mixture. 1.5 g of pure product is obtained. m.p. 102°–105° C.

EXAMPLE 4

6,6a,7,,8,9,10,10a,11-Octahydrodibenzo(b,e)oxepin-3-acetic acid (trans isomer).

(a) 11-Hydroxy-6,6a,7,8,9,10,10a,11-octahydrodibenzo(b,e)-oxepin-3-acetic acid.

14 g of sodium borohydride are added to a solution, cooled to −10° C. and placed under argon, of 34 g of 11-oxo-6,6a,7,8,9,10,10a,11-octahydrodibenzo(b,e)oxepin-3-acetic acid in 340 ml of absolute ethanol, and the mixture is allowed to return to room temperature while being stirred.

The mixture is poured into ice-cold water and evaporated, and the residue is taken up with water, which is washed with ether, acidified and extracted with ether.

After evaporation of the solvent, there remain 31 g of crystalline residue which is used in the stage (b) without further treatment.

(b) 6,6a,7,8,9,10,10a,11-Octahydrodibenzo(b,e)oxepin-3-acetic acid.

8.62 g of zinc iodide and 8.5 g of sodium cyanoborohydride are added at room temperature to a solution of 5 g of crude alcohol obtained according to 4(a) in 90 ml of 1,2-dichloroethane, and the mixture is left stirred for 2 h.

The mixture is poured into ice-cold water, acidified with 10% strength hydrochloric acid, dichloromethane is added and the mixture is left to outgas overnight. The organic phase is separated, dried and evaporated under vacuum, and this leaves 4.3 g of crystalline residue. 1.5 g of this is recrystallized in toluene, and 1.1 g of pure crystals is obtained. m.p. 175° C. (decomposition).

EXAMPLE 5

Laevorotatory enantiomer of 6,6a,7,8,9,10-hexahydrodibenzo(b,e)oxepin-3-acetic acid.

(a) 3-[(2-Carboxycyclohexyl)methoxy]benzeneacetic acid.

1.97 g (0.0856 mole) of sodium is dissolved in 50 ml of anhydrous methanol, and 6.52 g (0.0428 mole) of 3-hydroxybenzeneacetic acid are added under an argon atmosphere. The solvent is evaporated off and 7.2 g (0.0514 mole) of lactone of formula (VIa) are added to the salt thereby obtained. The mixture is heated to 195° C. for 45 min and allowed to cool, ice-cold water and 10% strength hydrochloric acid are added and the mixture is extracted with ether. After drying over magnesium sulphate, decolorization with vegetable charcoal and evaporation of the solvent, 13.64 g of oily residue are obtained, and this is used in the following stage without further treatment.

(b) 11-Oxo-6,6a,7,8,9,10,10a,11-octahydrodibenzo(b,e)oxe-pin-3-acetic acid.

120 g of polyphosphoric acid are added to 13.5 g of the oil obtained above, and the mixture is heated on an oil bath to 70° C. while being stirred. As soon as this temperature is reached, the heating is removed, since the temperature is maintained by itself.

When the reaction is complete, the mixture is poured into ice-cold water, extracted with ether and then with dichloromethane, the two organic phases are dried over magnesium sulphate and evaporated, and the residues are purified by chromatography on a silica column and the pure fractions are combined and distilled under vacuum. 1.15 g of a yellow oil is finally collected, and this is used in the following stage without further treatment.

(c) 11-Hydroxy-6,6a,7,8,9,10,10a,11-octahydrodibenzo(b,e)-oxepin-3-acetic acid.

1.15 g of the oil obtained above is dissolved in 15 ml of absolute ethanol, the solution is cooled to −10° C. and 0.47 g (0.0125 mole) of sodium borohydride is added under an argon atmosphere. The mixture is allowed to return to room temperature and, after 1 h, is poured into ice-cold water. The ethanol is evaporated off, the aqueous phase washed with ether, 2N hydrochloric acid is added and the product is extracted with ether. After drying over magnesium sulphate and evaporation under vacuum, 1 g of a colourless oil is obtained, and this is used in the following stage without further treatment.

(d) 6,6a,7,8,9,10-Hexahydrodibenzo(b,e)oxepin-3-acetic acid.

1 g of the oil obtained above is dissolved in 50 ml of anhydrous benzene, a few crystals of para-toluenesulphonic acid are added and the mixture is heated to reflux while the water is removed with a Dean and Stark apparatus.

When all the water has been removed, the solvent is evaporated off and the mixture is left to cool, and crystallizes.

0.6 g of crystals are separated by filtration, and these are recrystallized in benzene after being treated with vegetable charcoal. 0.27 g of pure enantiomer is finally obtained.

m.p. 137°–138° C. $[\alpha]^{20} = -28.27°$ (c=0.29; CHCl$_3$).

EXAMPLE 6

Dextrarotatory enantiomer of 6,6a,7,8,9,10-hexahydrodibenzo(b,e)oxepin-3-acetic acid.

(a) 3-[(2-Carboxycyclohexyl)methoxy]benzeneacetic acid.

8.2 g (0.355 mole) of sodium are dissolved in 100 ml of anhydrous methanol, and 27 g (0.18 mole) of 3-hydroxybenzeneacetic acid are added under an argon atmosphere.

The solvent is evaporated off and 30 g (0.214 mole) of lactone of formula (VIb) are added to the salt thereby obtained. The mixture is heated to 195° C. for 2 h, allowed to cool and poured into ice-cold water, the mixture is washed with ether, 10% strength hydrochloric acid is added to the aqueous phase and the product is extracted with ether.

After drying over magnesium sulphate and decolorization with vegetable charcoal, the solvent is evaporated off and 48 g of residue are obtained, and this is recrystallized in toluene. 22 g of crystals are finally collected, and these are used in the following stage without further treatment.

(b) 11-Oxo-6,6a,7,8,9,10,10a,11-octahydrodibenzo(b,e)oxe-pin-3-acetic acid.

220 g of polyphosphoric acid are added to 22 g of the crystals obtained above, and the mixture is heated in an oil bath at 75° C. for 30 min.

It is allowed to cool and poured into ice-cold water, the product is extracted with ether, the organic phase is dried over magnesium sulphate and the solvent evaporated off under vacuum. 15 g of orange-coloured foamy residue are obtained, and this is used in the following stage without further treatment.

(c) 11-Hydroxy-6,6a,7,8,9,10,10a,11-octahydrodibenzo(b,e)-oxepin-3-acetic acid.

15 g (0.0546 mole) of the product obtained above are dissolved in 300 ml of absolute ethanol, the solution is cooled to −10° C. and 6.2 g (0.163 mole) of sodium borohydride are added under an argon atmosphere.

The mixture is allowed to return to room temperature and, after 2 h, is poured into ice-cold water. The ethanol is evaporated off, the aqueous phases is washed with ether, 10% strength hydrochloric acid is added and the product is extracted with ether.

After drying over magnesium sulphate and evaporation under vacuum, 13 g of yellow foamy residue are obtained. This is ground in dichloromethane, giving 4.21 g of crystals which are used in the following stage without further treatment.

(d) 6,6a,7,8,9,10-Hexahydrodibenzo(b,e)oxepin-3-acetic acid.

4 g (0.0144 mole) of the crystals obtained above are dissolved in 200 ml of anhydrous benzene, 50 mg of para-toluenesulphonic acid are added and the mixture is heated under reflux while the water is removed with a Dean and Stark apparatus.

After 2 h, the clear solution obtained is concentrated to approximately 20 ml and purified without further treatment on a silica column, eluting with a 95:5 dichloromethane/methanol mixture. 3.17 g of beige crystals are recovered, and these are recrystallized in benzene, finally giving 2.36 g of shiny white crystals of pure enantiomer.

m.p. 136°–138° C. $[\alpha]_D^{20} = +29.21$ (c=0.38; CHCl$_3$).

EXAMPLE 7

α-Methyl-6,6a,7,8,9,10-hexahydrodibenzo(b,e)-oxepin-3-acetic acid.

(a) Methyl 6,6a,7,8,9,10-hexahydrodibenzo(b,e)oxepin-3-acetate.

A mixture of 5 g (0.0194 mole) of 6,6a,7,8,9,10-hexahydrodibenzo(b,e)oxepin-3-acetic acid and 50 ml of methanol, treated with a few drops of concentrated sulphuric acid, is heated under reflux for 1 h.

The mixture is evaporated to dryness, the residue taken up with water and neutralized with sodium carbonate, and the product extracted with ether.

After drying over magnesium sulphate and evaporation of the ether, 4.8 g of an oil are obtained, and this is purified by chromatography on a silica column, eluting with dichloromethane. 4.4 g of ester are collected, and this is used in the following stage without further treatment.

(b) Methyl α-methyl-6,6a,7,8,9,10-hexahydrodibenzo(b,e)oxepin-3-acetate.

4.44 ml of diisopropylamine are dissolved in 62 ml of tetrahydrofuran, the solution is cooled to −70° C. and 20.5 ml of 1.6M solution of n-butyllithium are introduced dropwise.

The mixture is stirred for 15 min and 4.3 g (0.0158 mole) of the ester obtained above, dissolved in 50 ml of tetrahydrofuran, are added dropwise. The mixture is stirred for 20 min and, still at −70° C., 2.64 g (0.0186 mole) of iodomethane are added.

Stirring is maintained for 1 h 30 min at −70° C., the mixture is then allowed to return to room temperature and poured into ice-cold water, the product is extracted with ethyl acetate and the organic phase is separated, dried over magnesium sulphate and evaporated. 4 g of an oil are obtained, and this is used in the following stage without further treatment.

(c) α-Methyl-6,6a,7,8,9,10-hexahydrodibenzo(b,e)oxepin-3-acetic acid.

4 g of the oil obtained above are dissolved in 25 ml of methanol, water and 6 ml of sodium hydroxide are added and the mixture is heated for 1 hour while evaporating off the methanol, and then for 2 hours under reflux.

The mixture is allowed to cool and is washed with ether, the aqueous phase is acidified and the precipitate extracted with ether. The ether phase is treated with vegetable charcoal, dried over magnesium sulphate, filtered and evaporated. The residue is recrystallized in cyclohexane and 3 g of pure product are finally collected. m.p. 143°–145° C.

The table on the following page illustrates the structures and physical properties of a few compounds according to the invention.

Biol. Med. 1962, 111, 544–547). The animals used are Charles River (France) male CD rats having an average weight of 120 to 130 g, distributed in batches at random using a distribution table.

The compounds are administered orally at doses of between 20 and 200 mg/kg, 1 hours before the injection of 0.1 ml of carrageenin, in a 1% strength suspension in sterile physiological saline, under the plantar aponeurosis of one of the hind paws. The control animals receive only placebo, a 1% strength solution of Tween 80 ®. The increase in volume of the paw is measured 3 hours after the injection of carrageenin by means of an Ugo Basile plethysmometer. The $AD_{40}$ dose, the dose of substance which decreases the volume of the oedema by 40% compared with the control animals, is determined graphically.

The oral $AD_{40}$ values of the compounds of the invention are between 1 and 50 mg/kg.

The analgesic activity of the compounds of the invention was demonstrated in the test of Koster et al (acetic acid "writhing test" in mice, Fed. Proc., 18, 412, 1959). Male $CD_1$ mice, fasted for 18 hours, are given the test compound, dissolved in Tween 80 ® at a concentration of 1%, orally in the proportion of 0.2 ml per 20 g of bodyweight; after 30 min, acetic acid (dissolved at a concentration of 0.6% in a mixture of carboxymethylcellulose and Tween 80 ®, in the proportion of 10 ml per kg of bodyweight) is administered intraperitoneally. In the control animals, this injection initiates, in the space of a few minutes, a syndrome of stretching movements and contortions (writhing) which may be regarded as the expression of a diffuse abdominal pain.

The total number od contortions are noted during 15

TABLE

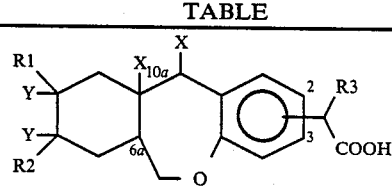

(I)

| Compound (Example) | Position —CHR3COOH | XX | YY | R1 | R2 | R3 | Config. 6a-10a | m.p.(°C.) |
|---|---|---|---|---|---|---|---|---|
| 1 (1) | 3 | — | HH | H | H | H | — | 145–147 |
| 1 (5) | | enantiomer (−) | | | | | — | 137–138 |
| 1 (6) | | enantiomer (+) | | | | | — | 136–138 |
| 2 (2) | 3 | — | — | H | H | H | — | 120–122 |
| 3 | 3 | — | — | CH3 | CH3 | H | — | 170–171 |
| 4 (3) | 3 | HH | HH | H | H | H | cis/trans (50/50) | 102–105 |
| 5 (4) | 3 | HH | HH | H | H | H | trans | 175(dec.) |
| 6 | 3 | HH | HH | H | H | H | cis/trans (80/20) | 100–103 |
| 7 | 2 | — | HH | H | H | H | — | 125–126 |
| 8 | 3 | HH | — | H | H | H | trans | 145–146 |
| 9 | 3 | HH | — | CH3 | CH3 | H | trans | 140–141 |
| 10 | 2 | HH | HH | H | H | H | cis/trans (50/50) | 88(dec.) |
| 11 (7) | 3 | — | HH | H | H | CH3 | — | 143–145 |

The compounds of the invention were subjected to various trials which demonstrated their value as substances having therapeutic, especially anti-inflammatory, applications.

Their acute toxicity is low, the oral lethal dose $LD_{50}$ in mice most frequently being more than 1,000 mg/kg.

For studying the anti-inflammatory activity, trials were performed using the test of carrageenin-induced oedema in rats according to the method of Winter et al ("Carrageenin-induced oedema in hind paw of the rat as an assay for anti-inflammatory drugs". Proc. Soc. Exp.

min, the percentage protection compared with the control batch is determined and the $AD_{50}$ (the dose which protects 50% of the animals) is calculated by a graphic method.

The oral $AD_{50}$ values of the compounds of the invention are between 75 and 170 mg/kg.

The results of the trials show that the compounds of the invention may be used as active substances of medicinal products and pharmaceutical compositions that are usable for the treatment of inflammation and pain of various origins.

For this purpose, they may be presented in all forms suitable for enteral or parenteral administration, for example the form of tablets, gelatin capsules, dragees, syrups, suppositories, suspensions to be taken orally or injectable suspensions, in combination with suitable excipients.

The daily dosage can range from 50 to 1000 mg of active substance.

We claim:

1. A compound, in the form of a pure optical isomer or a racemate, which is a dibenzo oxepinacetic acid of the formula (I)

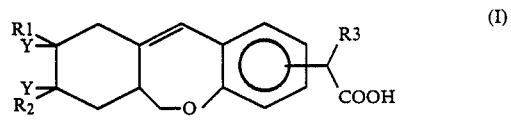

in which R1, R2 and R3, which may be the same or different, each represent hydrogen or methyl, and $CR_1Y$—$CR_2Y$ represents —$CR_1$=$CR_2$— or —$CHR_1$—$CHR_2$—, or a pharmaceutically acceptable salt thereof.

2. A compound according to claim 1, wherein R1, R2 and R3 each represent hydrogen, YY represents two hydrogen atoms and the group —CH(R3)COOH is at the 3-position.

3. An analgesic or anti-inflammatory pharmaceutical composition which comprises, as active ingredient, an effective analgesic or anti-inflammatory amount of a compound claimed in claim 1 in association with a pharmaceutically acceptable excipient.

* * * * *